United States Patent [19]

Partain, III et al.

[11] Patent Number: 4,929,722

[45] Date of Patent: May 29, 1990

[54] ACID DECRYSTALLIZATION OF AMINOPOLYSACCHARIDES AND DERIVATIVES THEREOF

[75] Inventors: Emmett M. Partain, III; George L. Brode, II, both of Bound Brook, N.J.

[73] Assignee: Union Carbide Chemicals and Plastics Company Inc., Danbury, Conn.

[21] Appl. No.: 189,312

[22] PCT Filed: Jun. 2, 1987

[86] PCT No.: PCT/US87/01246

§ 371 Date: Feb. 3, 1988

§ 102(e) Date: Feb. 3, 1988

[87] PCT Pub. No.: WO87/07618

PCT Pub. Date: Dec. 17, 1987

Related U.S. Application Data

[63] Continuation-in-part of Ser. No. 871,381, Jun. 6, 1986, abandoned.

[51] Int. Cl.⁵ .................. C08B 37/08; A61K 7/48; A61L 15/01
[52] U.S. Cl. .................. 536/20; 210/500.27; 424/59; 424/443; 424/444; 424/449; 514/55; 514/947; 514/953; 536/55.2

[58] Field of Search .............. 536/20, 55.2; 514/55, 514/947, 953; 424/443, 444, 449, 59; 210/500.27

[56] References Cited

U.S. PATENT DOCUMENTS

| | | | |
|---|---|---|---|
| 2,795,579 | 6/1957 | Doczi | 536/20 |
| 3,879,376 | 4/1975 | Vanlerberghe et al. | 536/20 |
| 3,953,608 | 4/1976 | Vanlerberghe et al. | 536/47 |
| 4,031,025 | 6/1977 | Vanlerberghe et al. | 424/47 |
| 4,424,346 | 1/1984 | Hall et al. | 536/20 |
| 4,528,283 | 7/1985 | Lang et al. | 536/20 |
| 4,542,014 | 9/1985 | Bresak et al. | 536/20 |
| 4,574,150 | 3/1986 | Austin | 536/20 |

FOREIGN PATENT DOCUMENTS

| | | |
|---|---|---|
| 59-106409 | 6/1984 | Japan. |
| 58-755561 | 1/1985 | Japan. |
| 2107340A | 4/1983 | United Kingdom. |

*Primary Examiner*—Ronald W. Griffin
*Attorney, Agent, or Firm*—Henry H. Gibson

[57] ABSTRACT

Heterogeneous acid decrystallization of aminopolysaccharides, especially chitosen, using diluent, organic acid and water, provides novel salts and covalent derivatives useful in diverse applications including biomedicine, personal care and fluid separation.

22 Claims, No Drawings

ACID DECRYSTALLIZATION OF AMINOPOLYSACCHARIDES AND DERIVATIVES THEREOF

CROSS REFERENCE TO RELATED APPLICATION

This application is a continuation-in-part of U.S. application Ser. No. 871,381, filed June 6, 1986, now abandoned.

FIELD OF THE INVENTION

This invention relates in general to a novel, inexpensive process for the decrystallization of aminopolysaccharides. In one aspect this invention is directed to a method for the heterogeneous, acid decrystallization of a particular aminopolysaccharide, chitosan. In a further aspect the invention is related to the preparation of various derivatives of the decrystallized product. In a still further aspect, the invention is directed to the use of such derivatives alone or in combination with other naturally occurring compounds for a wide variety of applications.

BACKGROUND OF THE INVENTION

Chitosan is a partially or fully deacetylated form of chitin, a naturally occurring polysaccharide. Structurally, chitin is a polysaccharide consisting of beta-(1→4) 2-acetamido-2-deoxy-D-glucose units, some of which are deacetylated:

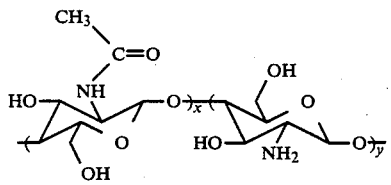

wherein x=0.85-0.95 and y=0.15-0.05. The degree of deacetylation usually varies between 8 and 15 percent, but depends on the species from which the chitin is obtained, and the method used for isolation and purification.

Chitin is not one polymer with a fixed stoichiometry, but a class of polymers of N-acetylglucosamine with different crystal structures and degrees of deacetylation, and with fairly large variability from species to species. The polysaccharide obtained by more extensive deacetylation of chitin is chitosan:

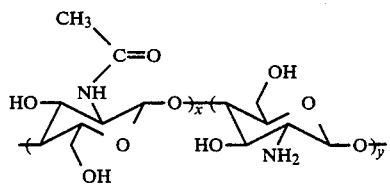

wherein x=0.50-0.10, and y=0.50-0.90.

Like chitin, chitosan is a generic term for a group of polymers of acetylglucosamine, but with a degree of deacetylation of between 50 and 90 percent. Chitosan is the beta-(1-4)- polysaccharide of D-glucosamine, and is structurally similar to cellulose, except that the C-2 hydroxyl group in cellulose is substituted with a primary amine group in chitosan. The large number of free amine groups (pKa=6.3) makes chitosan a polymeric weak base. Both chitin and chitosan are insoluble in water, dilute aqueous bases, and most organic solvents. However, unlike chitin, chitosan is soluble in dilute aqueous acids, usually carboxylic acids, as the chitosonium salt. Solubility in dilute aqueous acid is therefore a simple way to distinguish chitin from chitosan.

Chitosan is unique in that it is a polysaccharide containing primary amine groups. Chitosan and its derivatives are therefore useful materials in precious metal recovery, ion-exchange resins, surgical dressings and sutures, ocular bandages and lenses, and other applications in the biomedical field. Chitosan forms water-soluble salts with many organic and inorganic acids, and these chitosonium derivatives are useful in biomedical applications for several reasons.

First, as hereinafter indicated, these salts are biologically compatible with skin, hair, and most living tissues, and second, these chitosan salts are known to accelerate the healing process in damaged tissue. The tissue compatibility and healing acceleration of chitosan salts are also shared by covalent chitosan derivatives, covalent chitin derivatives, chitosan, and chitin.

However, prior to the present invention widespread use of chitosan derivatives had been limited because of the difficulty in their preparation. Chitosan is a highly crystalline polymer, and without rendering it amorphous and swollen with diluent, it cannot be easily derivatized. The methods known today to render chitosan reactive involve unusual, expensive, and toxic solvents such as dimethyl formamide or dimethyl sulfoxide, or expensive mechanical processes such as repetitive freezing of a chitosan slurry. In addition, while chitosan salt solutions may be prepared by dissolution of chitosan in dilute aqueous acids, such solutions are cumbersome because they must be very dilute, about five percent or less, to be pourable. Isolating the solid chitosan salt from these solutions requires expensive processes such as freeze-drying or spray drying, and these isolation techniques do not remove any unreacted acid which may not be desired in the final dried chitosan salt.

A variety of other methods have been reported in the literature for decrystallizing chitosan and most have not been entirely successful in decrystallizing the product without the need for expensive and time consuming procedures as outlined above.

For example, in 1957, U.S. Pat. No. 2,795,579 issued to Warner-Lambert Pharmaceutical Company and disclosed a process for the purification of chitosan which utilized salicylic acid. The method comprised forming an aqueous solution of an acid salt of crude chitosan, adding a soluble salicylate, separating the resulting precipitate of chitosan salicylate and regenerating the chitosan by decomposing the salicylate with a base. In the two examples in the patent, solutions of the crude chitosan were prepared by treatment with acid and dilution of the mixture with water. In example I of the patent the solution which contained less than 3 weight percent chitosan was indicated to be viscous.

Chitosan derivatives as sequestering agents for heavy metals are disclosed in U.S. Pat. No. 4,031,025 which issued June 21, 1977 and is assigned to L'Oreal of Paris, France. These derivatives are prepared by forming an aqueous solution of chitosan by reaction with hydrochloric acid and further reacting with a base and an anhydride. In Table I at column 6 of the patent the concentration in solution of chitosan in the eleven examples ranged from 2 to 5 weight percent.

U.S. Pat. No. 3,879,376 issued Apr. 22, 1975 and is also assigned to L'Oreal of Paris, France and disclosed and claimed certain chitosan derivatives. The derivatives disclosed were formed by the acylation of chitosan with a saturated or unsaturated organic diacid anhydride. It is stated in the patent that the chitosan acylation reaction is performed by adding a base diluted solution to an aqueous solution of a chitosan salt, alternately and in fractional amounts, to release the amine function and the acid anhydride. A divisional application issued as U.S. Pat. No. 3,953,608 on Apr. 27, 1976 and claims cosmetic compositions for the skin containing the chitosan derivatives.

United Kingdom patent application 2,107,340A, published Apr. 27, 1983, and assigned to Wella Aktiengesellschaft discloses certain surface active chitosan salts and their use in cosmetic applications. These salts are prepared by reacting chitosan and a surfactant in an aqueous or aqueous-alcohol solution. It is indicated in the patent that although solutions can be prepared in any desired quantity, for solubility reasons, a content of 0.05 to 10 weight percent is preferred. In example 1 deacetylated chitosan is dissolved in lauryl alcohol polyglycolethercarboxylic acid mixed with isopropanol and water to give a 4 weight percent solution which was indicated to be viscous. Other examples disclosed the preparation of solutions containing 0.5 to about 4 weight per cent chitosan salt.

In laid open Japanese patent publication Sho 59/1984 106409 of June 20, 1984 by Ichimaru Falcos K.K. Co. Ltd., cosmetic compositions were disclosed containing various kinds of chitin compounds including glycol chitin, carboxymethyl chitin and chitin sulfate. For example, it was indicated in this reference that the normally water-insoluble chitin is made soluble by glycolating chitin in the 6 position by a caustic soda treatment over a period of several days, followed by a freezing procedure, agitation with ethylene oxide and finally dialysis using a cellophane membrane.

In January, 1985, there was disclosed in Japanese patent 58/75561 by Ajinimoto K.K., wetting agents containing water soluble deacetylated non-crystalline chitin which contained 40–60 percent D-glucosamine units. Several compounds were disclosed for neutralization of the amino groups in the D-glucosamine units and included inorganic acids such as hydrochloric, sulfuric, phosphoric and organic acids such as acetic, citric, butyric, lactic, malic, succinic, gluconic, pyrrolidone carboxylic acid or acidic amino acids such as aspartic, glutamic, cysteine or homocysteine.

In U.S. Pat. No. 4,528,283 which issued July 9, 1985 to Gunter Lang et al. and is assigned to Wella Aktiengesellschaft of The Federal Republic of Germany, there are disclosed cosmetic compositions useful for the treatment of hair or skin and which contain certain glycerylchitosan macromolecular compounds. These novel compounds are prepared by reacting chitosan with glycidol at a temperature between 10° C. and 100° C. It is indicated in the patent that the chitosan is structurally modified before the reaction by precipitation and deep freezing. It is also stated in the patent that the few known water soluble derivatives of chitosan require expensive equipment and involved techniques in their production, and some are even known to be physiologically harmful.

A hair treating composition was patented by the Gillette Company as described in U.S. Pat. No. 4,542,014 and utilized in its formulations adducts of low molecular weight aminopolysaccharides derived from chitosan with hydrolyzed keratin protein. The patentee indicates in Example 1 that a 5 weight percent solution of low molecular weight chitosan became viscous when prepared.

Dry, free-flowing, water-soluble carboxylic acid complexes of chitosan are prepared as described in U.S. Pat. No. 4,574,150 to Austin, assigned to the University of Delaware, using a heterogeneous reaction system and select dispersant liquids and carboxylic acids. The patentee states that from zero to about 30 weight percent water based on the weight of the acid is used and demonstrates in Example 5 that large amounts of water are undesirable.

It will therefore be evident that while the prior art has succeeded in preparing water soluble derivatives and aqueous solutions of chitosan, it was only accomplished with great difficulty or the types of derivative were limited in number. For example, it is clearly demonstrated by the aforementioned art that attempts to prepare aqueous solutions of chitosan have been limited to those of very low concentration, since solubility and viscosity considerations do not permit the formation of solutions of solids content much above 5 weight percent chitosan. This, of course, is a decided disadvantage in the preparation of chitosan derivatives since, the low concentration of chitosan in solution will of necessity dictate a low concentration of the derivatized product. Moreover, notwithstanding the low solids content in aqueous solutions, the high viscosity renders such solutions largely unsuitable for chemical processing techniques utilizing an aqueous medium.

It has now been discovered that one way to obviate the problems of high solution viscosity and polymer recovery is to conduct the synthesis of aminopolysaccharide derivatives, particularly chitosan derivatives, by a heterogeneous process. Hence, it has now been found that chitosan can be conveniently decrystallized and derivatives prepared therefrom by a novel and inexpensive process hereinafter referred to as "acid decrystallization".

In the process of this invention chitosan is slurried in an appropriate diluent system containing water and an organic diluent, such as acetone. Addition of an acid, usually a carboxylic acid, provides a swollen, decrystallized slurry of the chitosan salt, which may be directly isolated by merely filtering and desiccating the solid. Derivatives prepared from the decrystallized chitosan can be either covalent or ionic (salts) compositions.

Accordingly, one or more of the following objects can be achieved by the practice of this invention. It is an object of this invention to provide a novel process for the acid decrystallization of chitosan. Another object of the invention is to provide a process for the decrystallization of chitosan which is simple and efficient. A further object of this invention is to provide a convenient and economically attractive process for the preparation of a variety of derivatives of chitosan. Another object is to provide such derivatives which have utility in the pharmaceutical, biomedical and personal care fields. These and other objects will readily become apparent to those skilled in the art in the light of the teachings herein set forth.

SUMMARY OF THE INVENTION

In its broadest aspect, the present invention is directed to a novel heterogeneous method for the acid decrystallization of aminopolysaccharides, particularly, chitosan, and to certain derivatives of chitosan. The method comprises the steps of:

(a) forming a mixture of a pulverulent, partially deacetylated aminopolysaccharide and
   (1) a diluent medium in which the aminopolysaccharide is swellable but essentially insoluble; the medium comprised of:
      (i) an inert, water soluble, polar organic diluent in which the aminopolysaccharide is insoluble and derivative of aminopolysaccharide is insoluble;
      (ii) at least one organic acid which is at least partially soluble in water, which is sufficiently acidic to form the ammonium salt of the aminopolysaccharide and yet not sufficiently acidic to cause hydrolysis of the aminopolysaccharide or derivative, and which is present in an amount sufficient to protonate the reactive sites of the deacetylated aminopolysaccharide; and
   (2) water in an amount generally in excess of the amount of organic acid and up to about 65 weight percent of said medium;
(b) agitating the mixture at a temperature and for a period of time to effect at least partial decrystallization; and
(c) recovering the aminopolysaccharide derivative from the mixture.

As previously indicated, a variety of derivatives of decrystallized aminopolysaccharides, such as chitosan, can be prepared. These derivatives can be ionic compositions (salts) or covalent compositions.

To prepare covalent chitosan derivatives such as esters, amides and ethers, the swollen, decrystallized slurry of the chitosan salt prepared by the aforementioned method, is causticized with a stoichiometric excess of a base such as sodium hydroxide and then reacted with various electrophiles.

To prepare ionic derivatives in the form of salts of chitosan, the acid used in the decrystallization step can be chosen so that the desired functional group and both decrystallization and derivatization, i.e., salt formation, is accomplished simultaneously.

DETAILED DESCRIPTION OF THE INVENTION

As indicated above, the present invention provides a novel, heterogeneous method for the decrystallization of aminopolysaccharides and to a variety of derivatives having properties which render them particularly attractive for use in the biomedical field.

The method of the present invention differs from the methods disclosed in the literature in several respects. First, the acid decrystallization process of this invention does not involve dissolving the aminopolysaccharide, such as chitosan, in an aqueous medium. Since chitosan is a very rigid molecule, only a very limited quantity can be rendered water soluble before the solution becomes too viscous to be easily handled. If the solution is further diluted to overcome the viscosity problem, the concentration of chitosan is reduced even further and hence any chemical reactions to derivatize the molecule are very inefficient and economically unattractive.

For example, in literature currently available by a company engaged in the commercial sale of chitosan in the United States, it is indicated that chitosan is soluble in aqueous solutions of most acids, particularly organic acids such as formic acid, malic, tartaric, citric, adipic, and the like. It is further indicated that in order to make a one percent solution of chitosan in water, chitosan is mixed with water and then an equal volume of inorganic acid solution is added. For concentrated solutions of chitosan, which are indicated in the literature reference to be from about 2 to 4 percent by weight, an equal weight of acid to that of the chitosan is employed. With inorganic acids such as hydrochloric or nitric acids chitosan is soluble within the range of 0.15 to 1.1 percent acid by weight. Chitosan is not soluble in sulfuric acid and has only marginal solubility in phosphoric acid at concentrations below 0.5 percent.

Thus, prior to the present invention, no method having widespread applicability was reported in the literature whereby aminopolysaccharides could be decrystallized and derivatized in economically attractive quantities by a simple and efficient process.

The method of this invention, effects decrystallization and derivatization of aminopolysaccharides such as chitosan, using an organic acid in a diluent medium in which the chitosan is swellable but essentially insoluble.

A variety of acids can be used in the decrystallization process of this invention. It is, of course, necessary that the acid be at least partially soluble in water, be sufficiently acidic to form the ammonium salt of the aminopolysaccharide and yet not sufficiently acidic to cause hydrolysis of the aminopolysaccharide or derivative, and which is present in an amount sufficient to protonate the reactive sites of the deacetylated aminopolysaccharides. Such acids can be represented by the formula:

$$R\text{-}(COOH)_n$$

wherein n has a value of 1 or 2 and R represents a mono- or divalent organic radical composed of carbon, hydrogen and optionally at least one of oxygen, nitrogen and sulfur. Preferred acids are the mono- and dicarboxylic acids composed of carbon, hydrogen, oxygen and nitrogen, and which are at least partially water soluble, biologically and/or pharmaceutically acceptable for use on the human body in such formulations for the treatment or conditioning of skin, hair, eyes and the like.

Accordingly, a wide variety of acids can be employed which not only affect decrystallization of chitosan, but simultaneously afford desirable derivatives as well. Illustrative acids, in addition to those previously mentioned include, among others, formic, acetic, N-acetylglycine, acetylsalicylic, fumaric, glycolic, iminodiacetic, itaconic, DL-lactic, maleic, DL-malic, nicotinic, 2-pyrrolidone-5-carboxylic, salicylic, succinamic, succinic acid, ascorbic, aspartic, glutamic, glutaric, malonic, pyruvic, sulfonyldiacetic, thiodiacetic and thioglycolic acids.

As indicated above, the medium employed in the decrystallization of the chitosan is a combination of water and an organic compound. This diluent system which is employed in the decrystallization process of the present invention is a combination of water and an organic compound. Organic compounds which are useful in the present invention are those which are water-soluble, in which the aminopolysaccharide is insoluble, and in which the aminopolysaccharide derivative is insoluble. Illustrative organic compound which can be employed include ketones such as acetone; alcohols such as methanol, ethanol, n-propanol, isopropanol, t-butanol; acetonitrile; tetrahydrofuran; dioxane; 2-ethoxyethanol; dimethoxyethane and the like.

The second component of the diluent medium is water and it is employed in an amount generally in excess of the amount of organic acid and up to about 65, and preferably up to about 45, weight percent of the total medium, i.e., the total of the water plus the organic compound. In practice, optimum results are obtained when the diluent medium contains from about 30 to about 45 weight percent water and more preferably about 40 weight percent.

In contrast to the teachings of the prior art the method of the present invention avoids formation of a chitosan solution. By the process of the present invention the chitosan is caused to swell and accordingly viscous solutions containing only a few percent of chitosan are avoided.

The sequence of mixing the diluent medium and the deacetylated chitosan is not necessarily critical. However, it has been observed that excellent results are obtained if the diluent medium is prepared from the water and organic compound together with the acid and then the chitosan added.

As previously indicated chitosan has a very rigid structure and when it dissolves in acid solution it provides a very viscous product of low concentration of chitosan. In order for chitosan to be soluble at all, it must have a relatively large number of free primary amine groups. The chitosan employed in the present invention is deacetylated chitin and the degree of deacetylation is normally in excess of 60 percent and preferably in excess of 75 percent.

The molecular weight range of the chitosan employed in the present invention can range from 10,000 to several million and more preferably from about 100,000 to about 5 million. Particularly preferred is chitosan having a molecular weight of from about 300,000 to about 2.5 million.

Thus, using acids of the aforementioned formula the method of the present invention can be employed in the preparation of a variety of derivatives of chitosan having utility in the above-mentioned fields. For example, it is known that salts of pyrrolidone carboxylic acid (PCA) are effective moisturizing agents, have a low order of irritation and accordingly are useful in the biomedical field.

Any number of chitosan derivatives that require alkali chitosan in the process may be made by the method of the present invention. Modification may occur at the 6 hydroxyl, the 3 hydroxyl, or the 2 amine, or any combination thereof, but in the reactions set forth below the modification is shown in the 2 position. In each case, the chitosan is swollen and activated by the process described above.

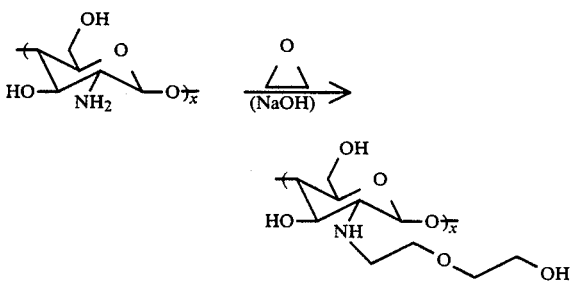

Glycol chitosan is a water soluble non-ionic chitosan prepared from ethylene oxide as indicated in the above equation. The amine may be further reacted to give quats.

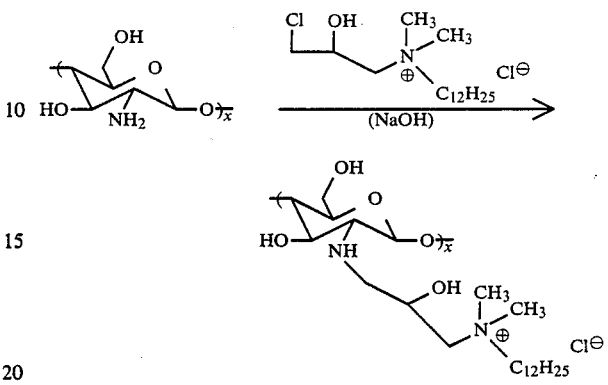

Reaction with epi-amine 342, i.e., 3-chloro-2-hydroxypropyl-N-dodecyl-N,N-dimethylammonium chloride as indicated above, yields a hydrophobe-modified quaternary chitosan polymer. Such a polymer has use in the personal care applications field. This reaction is applicable to other chlorohydrin quats such as epi-amine 188, i.e., 3-chloro-2-hydroxypropyl trimethylammonium chloride, and epi-amine 151, i.e., glycidyl trimethylammonium chloride.

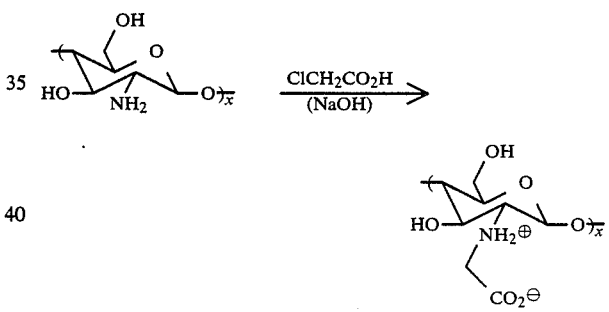

Preparation of carboxymethylchitosan as above, gives a unique polymeric amphoteric for many uses, including biomedical applications. These materials structurally approach hyaluronic acid, and possess many of the same useful properties. Amides may also be prepared from anhydrides such as maleic anhydride and succinic anhydride.

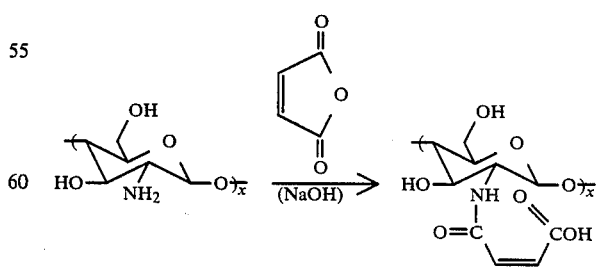

The present invention provides a salt of chitosan and pyrrolidone carboxylic acid, i.e., PCA, which salt has a large number of useful applications such as burn treatment, topical medical formulation for rashes and fungal infections. While chitosan accelerates healing the PCA is a built-in humectant.

As indicated in the examples, such a polymer is prepared by reacting a finely ground slurry of chitosan with PCA in a polar solvent such as aqueous ethanol, or other suitable solvent that will dissolve PCA:

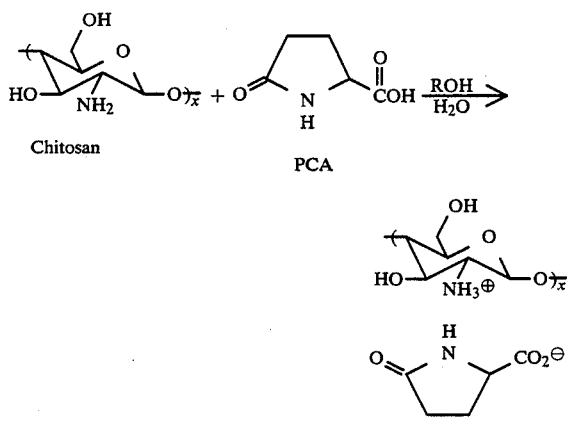

This method for preparing chitosan salts is applicable to other organic acids that are soluble in polar organic solvents such as ethanol. For example, thioglycolic acid in aqueous ethanol can be reacted with chitosan to give the thioglycolate salt, which has use in the biomedical field since thioglycolate is a natural component of hair:

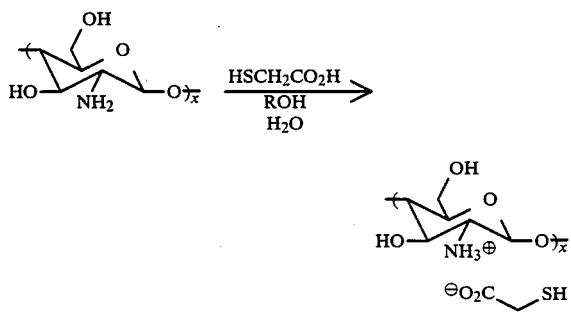

Novel chitosan derivatives of the present invention include various salts and/or covalent derivatives of chitosan. These derivatives can be prepared by the method of the present invention or using known procedures such as by freeze-drying, spray-drying, non-solvent precipitation, dry blending, or the like. Chitosan salts of the present invention include the salts of one or more of the following acids: 2-pyrrolidone-5-carboxylic; itaconic; and acidic vitamins such as nicotinic, i.e., niacin, ascorbic, retinoic, folic, biotin and pantothenic. Covalent chitosan derivatives of the present invention include the products of causticized chitosan and various electrophiles including one or more of the following: ethylene oxide; propylene oxide; glycidol; 3-chloro-1,2-propanediol; methyl chloride; ethyl chloride; isatoic anhydride; succinic anhydride; γ-butyrolactone; β-propiolactone; 1,3-propanesultone; acrylamide; glycidyltrimethylammonium chloride; glycidyldimethyl alkylammonium chloride, such as lauryl; sodium chlorosulfonate; dimethyl sulfate; sodium chloroethanesulfonate; sodium chloroacetate; or chloroacetic acid; alkyl phenyl glycidyl ethers; 1,2-epoxy dodecane; and the like. The chitosan derivative may be either water-soluble or rendered water-insoluble, by, for example, thermal treatment and/or using a cross-linking agent, which may be incorporated into the derivative.

Chitosan derivatives have a wide variety of uses in such diverse fields including: as films; woven or nonwoven sheets; fibers; membranes, such as in fluid separating including gas and/or liquid purification; biomedical applications such as bandages, wound dressings, catheters, medical appliance coatings, controlled-release technology, drug delivery systems, sutures, artificial skin, ophthalmic applications; personal care applications and the like. For example, the chitosan salt of 2-pyrrolidone-5-carboxylic acid, (chitosonium pyrrolidone carboxylate), is useful as a humectant in personal care applications and is expected to have utility in film form as a burn and wound dressing. The salt is also a potential synthetic hyaluronic acid substitute, with many applications in the biomedical field. Chitosonium salicylate is useful as a sunscreen. A thermally cured film of chitosonium itaconate would be useful in biomedical slow release technology and may also be useful as a bandage or wound dressing.

Moreover, the healing properties of chitin and chitosan are known. In addition to being effective fungicides, these polysaccharides are useful in accelerating the healing rate of wounds. For example, chitosonium acetate had been used as a burn covering. A solution is sprayed on the burn, forming a covering to protect the injury, while being permeable to oxygen and speeding the healing of the burn. For typical applications requiring a water-soluble form of chitosan, chitosonium acetate is employed.

When free of its naturally-associated proteins, chitin is not antigenic to human tissue, and may be used on, or inserted under the skin, or placed in contact with body fluids without harm. Chitin in the body is slowly attacked by lyzozyme and is absorbed. In addition chitin and chitosan may be safely ingested by humans, for example, common foods such as bread, beer, wine, shrimp, crabs and mushrooms all contain some chitin.

Glycosaminoglycans (GAGS) are a class of polysaccharides that occur in the connective tissue of mammals, and include hyaluronic acid, chondroitin sulfate, and heparin. Some of these polysaccharides, hyaluronic acid in particular, have been used successfully to accelerate wound healing and tissue regeneration in both humans and laboratory animals.

The exact mechanism of accelerated tissue regeneration is not know, but oligomeric metabolites of N-acetylglucosamines and glucosamine functionality present in glycosaminoglycans such as hyaluronic acid is present in chitin and chitosan, and similar accelerated wound healing and tissue regeneration properties have been reported for chitin and chitosan.

Moreover, it has been reported in the literature that growth inhibition of *Pseudomonas aeruginosa*, *Staphylococcus aureus*, and *Staphylococcus epidermis* on agar plates were noted with 1% chitosan solutions in dilute acetic acid. Parallel experiments with the fungus *Candida tropicalis* and chitosan solutions also exhibited fungal growth inhibition. Similar results were reported on the fungistatic action of chitosan on plant pathogens.

Native chitin has a hygroscopicity of 8.9% bound water, which is similar to that of mercerized cellulose fibers. There is little reported work on the humectancy of chitosan and chitin derivatives but ethylated chitin is reported to be highly hygroscopic and hence ionic chitosan derivatives would therefore be expected to be even more efficient in binding water because of electrostatic and hydrogen bonding interactions. Further, the ionic chitosan derivatives are structurally similar to glycosaminoglycans such as hyaluronic acid, which has a high degree of humectancy and accordingly can be employed as a substitute for, or blended with such compounds.

The following examples are illustrative:

EXAMPLE 1

PREPARATION OF CARBOXYMETHYLCHITOSAN BY THE ACID DECRYSTALLIZATION PROCEDURE

A 500 ml, four-necked round bottom flask, was fitted with a stirring rod and paddle, a serum cap, a subsurface nitrogen feed, and a claisen head fitted with a pressure-equalizing addition funnel and an Allihn condenser with a mineral oil bubbler. The flask was charged with 10 g of chitosan (ground to pass a 0.5 mm screen), 46 ml of isopropanol, and 24 ml of water. While stirring the slurry, it was purged with nitrogen for 40 minutes to remove entrained oxygen.

A solution of 6.0 g of glacial acetic acid in 25 ml of isopropanol was added dropwise to the slurry over a 5 minute period, followed by 15 ml of water. The swollen chitosan slurry was then stirred under nitrogen for 30 minutes. Thereafter 26.82 g of 50% aqueous sodium hydroxide was added by syringe dropwise to the slurry under nitrogen, and the causticized slurry was stirred for 90 minutes.

A solution of 11.2 g of monochloroacetic acid in 25 ml of isopropanol was added to the slurry, and the mixture was refluxed for four hours under nitrogen. The slurry was then cooled to room temperature and neutralized with a solution of 1.5 g of glacial acetic acid in 25 ml of isopropanol. The polymer was collected by vacuum filtration, and washed in a Waring blender, four times with pure acetone. The polymer was dried in vacuo at 50° C. to give a granular olive-grey solid, 19.62 g, which was readily soluble in water to give a solution free of insolubles. The polymer was also soluble in dilute aqueous sodium hydroxide and aqueous acetic acid.

As a control experiment, the above procedure was repeated exactly, except that the 6.0 g of glacial acetic acid used in the acid decrystallization step was omitted, and the caustic charge was correspondingly reduced from 25.82 g to 18.82 g of 50% aqueous sodium hydroxide. The resulting olive-grey solid, (18.82 g) was found to be swollen but not soluble in water, dilute aqueous sodium hydroxide, or dilute aqueous acetic acid. These experiments demonstrate the use of acid decrystallization in preparing completely water-soluble covalent derivatives of chitosan by a heterogeneous process.

EXAMPLE 2

PREPARATION OF 2-PYRROLIDONE-5-CARBOXYLATE DERIVATIVE

In this example, 2-pyrrolidone-5-carboxylic acid, hereinafter referred to as PCA, was prepared and mixed with chitosan in varying ratios. 3.36 g of PCA was dissolved in 75 ml of absolute ethanol. Three 125-ml Erlenmeyer flasks were charged with 2.5 g of 0.5 mm mesh chitosan having a degree of deacetylation of about 0.80, and 37.5 ml, 25 ml, and 12.5 ml of the alcoholic PCA solution were added to each, respectively, and the slurry diluted to 50 ml with absolute ethanol. Each slurry was stirred for 2 hours. The molar ratios of the three solutions were respectively 1:1, 0.67:1, and 0.33:1 of PCA to chitosan.

Each slurry was vacuum-filtered and the residue was washed with pure acetone. The mass of each batch of product was 2.5 g, and the product was completely water insoluble. The product had the characteristics and behavior of native, unreacted chitosan.

The three 2.5 g recovered chitosan samples were combined and placed in a 250-ml beaker with 100 ml of 95% ethanol (7.5 g in 100 ml).

3.5 g of PCA were dissolved in 16 ml of water, and the acid solution was added to the ethanol slurry of chitosan (7.5 g). The chitosan became swollen and curd-like. The slurry was stirred for a few minutes, and 80 ml of 95% ethanol were added. The curd-like polymer settled, and the slurry was vacuum-filtered. By the consistency of the polymer, recovery could be made by either decantation or centrifugation. The polymer was then washed three times with pure acetone to desiccate it. The polymer was placed in a tared crystallizing dish and dried in vacuo overnight at 50° C. A small portion of polymer was checked for water-solubility before vacuum drying and found to be soluble. A small amount of insoluble material remained suspended in solution. The pH of the solution was 6.0.

EXAMPLE 3

PREPARATION OF CHITOSONIUM PYRROLIDONE CARBOXYLATE

A 500 ml flask was fitted with a stirring paddle and motor, and charged with 10.0 g of chitosan (degree of deacetylation about 0.80, ground to 0.5 mm mesh) and 100 ml of acetone. A slurry of 8.0 g of DL-2-pyrrolidine-5-carboxylic acid in 33 ml of water was added, followed by 43 ml of acetone and 35 ml of water. The slurry was stirred for one hour.

The slurry was vacuum-filtered, and the polymer was washed in a Waring blender once with 300 ml of 4:1 (by volume) acetone/water, and twice with pure acetone. The polymer was a granular greenish-grey solid, which was dried in vacuo at 50° C. to yield 16.5 g of product. Correcting for volatiles in the starting material and product, the mass gain MS of chitosonium pyrrolidone carboxylate was found to be 0.82. The polymer was readily soluble in water to give a clear, amber solution with no insolubles. Brookfield viscosity (1% solution)=660 cP (30 rpm, Spindle#2).

EXAMPLE 4

PREPARATION OF CHITOSONIUM ITACONATE

A 600 ml beaker was fitted with a stirring paddle and motor, and charged with 15.0 g of chitosan (degree of deacetylation about 0.80, ground to 0.5 mm mesh), 180 ml of water, and 120 ml of acetone. While stirring the slurry, 12.1 g of itaconic acid (Aldrich) was added as a powder over a few minutes. The slurry was then stirred for three hours.

The slurry was allowed to settle, and 300 ml of supernatant was decanted. Fresh acetone (225 ml) was added, the slurry was stirred for 15 minutes. The polymer was collected by vacuum filtration, and dried in vacuo at 50° C. to yield 19.0 g of product. Correcting for volatiles in the starting material and product, the mass gain MS of chitosonium itaconate was found to be 0.30. Chitosonium itaconate is insoluble in water at room temperature, but dissolves at elevated temperature (about 75° C.), and remains dissolved after cooling.

EXAMPLE 5

PREPARATION OF CHITOSONIUM SALICYLATE

A 250 ml beaker was fitted with a stirring paddle and motor, and charged with 3.0 g of chitosan (degree of deacetylation about 0.80, ground to 0.5 mm) and 25 ml of isopropanol. A solution of 2.45 g of salicylic acid and 24 ml of isopropanol was added to the slurry, followed by 15 ml of water. The slurry began to thicken and swell. After stirring for several minutes, the thick, sticky slurry was placed in a Waring blender and desiccated with acetone (2 x 250 ml). The polymer was collected by vacuum filtration and dried in vacuo at 50° C., yield 4.23 g of product. The polymer was partly soluble in water at room temperature, but dissolves at elevated temperatures (about 75° C.), and thereafter remains completely soluble after cooling to room temperature.

EXAMPLE 6

PREPARATION OF OTHER CHITOSONIUM DERIVATIVES

In a manner similar to that employed in the above examples, and using the basic procedure described for chitosonium pyrrolidone carboxylate, other chitosonium salts were prepared. These salts were readily soluble in water at room temperature, except for the malate, maleate, itaconate, salicylate, tartarate, fumarate, and succinate salts which required heating at about 75° C. to effect dissolution. The product from the reaction of glyoxylic acid is insoluble in water, presumably because of Schiff base formation as described by R. A. A. Muzzarelli and F. Taufani (Pure & Appl. Chem., 54 (11), 2141 (1982)). The products from the reaction of acrylic, citric, gallic, 4-hydroxybenzoic, methacrylic, and vanillic acids are only slightly soluble in water, because of limited reaction efficiencies, as indicated in the low mass gain DS values for these products. The results are set forth below in Table 1:

TABLE 1

CHITOSONIUM DERIVATIVES OF ORGANIC ACIDS

| Acid | Diluent | % H$_2$O | Mass Gain DS[1] | pKa |
|---|---|---|---|---|
| Acetic | Acetone | 32 | 0.25 | 4.8 |
| N-Acetyl-L-cysteine | Isopropanol | 38 | 0.37 | |
| N-Acetyl glycine | Acetone | 32 | 0.80 | 3.6 |
| Acetylsalicylic | " | 32 | 0.51 | 3.4 |
| Acrylamido-2-methane sulfonic | " | 32 | 0.86 | |
| Acrylic | " | 32 | 0.34 | 4.3 |
| Adipic | Isopropanol | 38 | 0.47 | 4.4,5.3 |
| L-Aspartic | Isopropanol | 38 | 0.86 | 1.9,3.7 |
| Citric | " | 81 | (0.2) | 3.0,4.4,5.7 |
| Fumaric | " | 32 | 0.33 | |
| 2-Furoic | Isopropanol | 35 | 0.64 | 3.2 |
| Gallic | Acetone | 82 | 0.27 | 3.1,8.8 |
| L-Glutamic | " | 56 | 0.96 | 2.1,4.3 |
| Glutaric | " | 32 | 0.31 | 4.3,5.4 |
| Glycolic | " | 32 | 0.74 | 3.7 |
| Glyoxylic | " | 31 | 0.55 | 3.5 |
| Hydrochloric | " | 34 | 0.80 | |
| 4-Hydroxybenzoic | Isopropanol | 38 | 0.15 | 4.7,9.4 |
| Iminodiacetic | Acetone | 31 | 0.54 | 3.0,9.9 |
| Itaconic | " | 65 | 0.34 | 3.6,5.0 |
| 3-Ketoglutaric | Isopropanol | 35 | 0.51 | |
| DL-Lactic | Acetone | 32 | 0.77 | 4.5 |
| Maleic | " | 32 | 0.43 | 1.8,6.1 |
| DL-Malic | " | 65 | 0.46 | 3.5,5.1 |

TABLE 1-continued

CHITOSONIUM DERIVATIVES OF ORGANIC ACIDS

| Acid | Diluent | % H$_2$O | Mass Gain DS[1] | pKa |
|---|---|---|---|---|
| Malonic | " | 32 | 0.49 | 2.8,5.7 |
| Methacrylic | " | 32 | 0.16 | 4.7 |
| Methanesulfonic | Isopropanol | 38 | 0.80 | |
| Nicotinic (Niacin) | " | 24 | 0.64 | 4.9 |
| Oxiniacic | " | 38 | 0.70 | |
| Picolinic | " | 35 | 0.50 | 5.3 |
| 2,3-Pyridinedicarboxylic | " | 38 | 0.58 | 2.4,4.8 |
| 2-Pyrrolidone-5-carboxylic | Acetone | 32 | 0.86 | |
| | Isopropanol | 38 | 0.82 | |
| Pyruvic | Acetone | 32 | 0.40 | 2.4 |
| Saccharin | Isopropanol | 38 | 0.86 | 1.3 |
| Salicyclic | Ethanol | 20 | 0.70 | 3.0 |
| Succinamic | Acetone | 32 | 0.67 | 4.5 |
| Succinic | " | 65 | 0.41 | 4.2,5.7 |
| Sulfamic | Isopropanol | 38 | 0.84 | |
| Sulfanilic | " | 38 | (0.75) | 3.3 |
| Sulfonyldiacetic | Acetone | 32 | 0.45 | |
| L-Tartaric | Isopropanol | 38 | 0.58 | 2.9,4.2 |
| Thioacetic | Acetone | 32 | 0.19 | 3.6,10.2 |
| Thiolactic | " | 32 | 0.57 | 3.6,10.2 |
| Vanillic | Isopropanol | 40 | 0.20 | 4.5,9.4 |

[1]DS = degree of substitution (measured by mass gain)

EXAMPLE 7

FILMS CAST FROM CHITOSONIUM ITACONATE

A 4 percent solution of chitosonium itaconate was prepared by heating and stirring a mixture of 4 g of chitosonium itaconate and 96 g of water at 75° C. The solution was cooled, and a film was cast (25 mil thick) on a metal plate using a doctor knife. After allowing the solvent to evaporate, the film was removed from the plate. This film was readily soluble in water. However, after thermally curing the film at 100° C. for several hours, the film was found to be insoluble in water, even boiling water for one hour.

Similar thermal curing behavior was noted with chitosonium fumarate, lactate, 2-pyrrolidone-5-carboxylate, pyruvate and succinate.

EXAMPLE 8

CHITOSONIUM SALICYLATE SUNSCREEN SKIN CREME

Chitosonium salicylate (1.0 g, prepared as described in example 5) was mixed with 78.0 g of distilled water, and heated to 60° C. until all of the polymer had dissolved. Propylene glycol (10.0 g) was added, with stirring at 60° C. Separately, a solution of cetyl alcohol (6.0 g), stearic acid (3.0 g), silicone oil 7002 (1.0 g, from Union Carbide), and TWEEN 20 (1.0 g, from ICI, Inc.) was prepared at 60° C., and while stirring vigorously, this solution was added to the aqueous chitosonium salicylate solution at 60° C. After stirring for five minutes, the agitation was stopped, and the mixture was allowed to cool to give a white skin creme. The UV absorbance spectrum of chitosonium salicylate exhibits a maximum at 298 nm ($\epsilon = 3.6 \times 10^3 M^{-1} cm^{-1}$), which is in the center of the UV-B region (320-290 nm). Therefore chitosonium salicylate is an effective sunscreen agent.

EXAMPLE 9

PREPARATION OF CHITOSONIUM ITACONATE FILMS IMPREGNATED WITH SULFANILAMIDES

A solution of chitosonium itaconate was prepared by dissolving 0.66 g of chitosonium itaconate (prepared as described in example 4) in 17 ml of distilled water at 60° C. After cooling to room temperature, a solution of 0.022 g of sulfanilamide in 2 ml of distilled water was added and thoroughly mixed. A film was cast with this solution as described in example 8, and the film was cured at 100° C. for 18 hours. The cured film (3% sulfanilamide by weight) was insoluble in water, but over 95% of the impregnated sulfanilamide was extracted from the film in water after 30 minutes (measured by a Beckman 35 spectrophotometer, $\lambda max = 262$ nm, $\epsilon = 1.61 \times 10^4 M^{-1} cm^{-1}$). The presence of sulfanilamide does not impair the thermal curing of the chitosonium itaconate film, and the sulfanilamide is extracted from the cured film unaltered. Sulfanilamide is an example of a topical antibacterial drug which can be impregnated in chitosonium itaconate films for slow release. Films of sulfanilamide containing chitosonium itaconate can be used as wound dressings to deliver a steady, controlled amount of sulfanilamide to the wound.

EXAMPLE 10

PREPARATION OF CHITOSONIUM PYRROLIDONE CARBOXYLATE MOISTURIZING CREME

Chitosonium pyrrolidone carboxylate (1.0 g, prepared as described in example 3 was dissolved in 78.0 g of distilled water. The solution was heated to 60° C. and 10.0 g of propylene glycol was added with stirring. Separately, a solution of cetyl alcohol (6.0 g), stearic acid (3.0 g), silicone oil 7002 (1.0 g, from Union Carbide), and BRIJ 98 (1.0 g, from ICI, Inc.) was prepared at 60° C. and while vigorously stirring, this solution was added to the aqueous chitosonium pyrrolidone carboxylate solution at 60° C. After stirring for five minutes, the agitation was stopped, and the mixture was allowed to cool to give a white, moisturizing skin creme, to condition skin and accelerate healing of damaged skin.

EXAMPLE 11

PREPARATION OF CHITOSONIUM PYRROLIDONE CARBOXYLATE-HYALURONIC ACID BLENDS AS WOUND DRESSINGS

A solution (50 g) of 0.1% (by weight) commercial, extraction grade sodium hyaluronate was ion-exchanged by stirring with 5 g of AMBERLITE 200 ion exchange resin for 1 hour. The resin was removed by vacuum filtration. A solution (45 ml) of 1% (by weight) chitosonium pyrrolidone carboxylate in distilled water was place in a 100 ml Waring blender, and stirred at a rate of 3000 rpm. While vigorously mixing the chitosonium pyrrolidone carboxylate solution, 45 ml of ion-exchanged sodium hyaluronate were added by syringe over one minute and the mixture was stirred at 3000 rpm for two minutes. The product was a highly viscous, very slightly milky, homogeneous blend of chitosonium pyrrolidone carboxylate and hyaluronic acid which is useful as a wound dressing or coating to protect tissues and accelerate healing.

If the two polymer solutions are mixed in reverse order (chitosonium pyrrolidone carboxylate added to hyaluronic acid) or the stirring rate is insufficient to give a good mixing, the chitosonium pyrrolidone carboxylate/hyaluronic acid blend is rendered insoluble and precipitates.

The procedure above was repeated with commercial, fermentation grade sodium hyaluronate with the same results. In both cases, the ion exchange step may be omitted, but the resulting homogeneous chitosonium pyrrolidone carboxylate/sodium hyaluronate blends are somewhat more opaque.

EXAMPLE 12

PREPARATION OF FILMS OF CHITOSONIUM PYRROLIDONE CARBOXYLATE/HYALURONIC ACID BLENDS

A blend of 10 parts of chitosonium pyrrolidone carboxylate and 1 part of hyaluronic acid was prepared as described in example 11. A film of the highly viscous blend was obtained using a doctor knife and metal plate as described in example 7. The solvent was allowed to evaporate at 25° C. over 72 hours resulting in a highly flexible, clear film that could be removed from the plate.

Although the invention has been illustrated by the preceding examples it is not to be construed as being limited to the materials employed therein, but rather, the invention is directed to the generic area as herein before disclosed. Various modifications and embodiments thereof can be made without departing from the spirit or scope thereof.

EXAMPLE 13

INSOLUBILIZATION OF CHITOSONIUM PYRROLIDONE CARBOXYLATE FILMS

Films of chitosonium pyrrolidone carboxylate can be rendered insoluble using two methods. In both cases, the resulting films are insoluble in water, even upon boiling for 30 minutes. Such films may have utility in such areas as wound and burn dressings, sutures, catheters, gauze, ocular bandages, cosmetic masks, pharmaceutical carriers, drug delivery systems, microencapsulation, transdermal patches, dialysis membranes, gas or liquid separation membranes, and food wrapping.

Method A

A 2 mil thick chitosonium pyrrolidone carboxylate film is heated in an oven at ambient pressure and 100° C. for 1 to 2 hours. The film was then removed from the oven and cooled, and found to be water insoluble, as described above. Heating the polymer film at 100° C. for about 2 hours improves the relative strength of the film in water.

Method B

A 2 mil thick chitosonium pyrrolidone carboxylate film is placed in a Soxhlet extractor and extracted with absolute ethanol for 18-24 hours. The film was then recovered from the Soxhlet extractor, and it was found to be insoluble in water, as described above.

In both cases, before the insolubilization process, the films of chitosonium pyrrolidone carboxylate were readily soluble in cold water.

EXAMPLE 14

MOISTURE ABSORPTION TESTING OF CHITOSONIUM POLYMERS

To evaluate the humectancy of chitosonium polymers, the following test procedure was used. Approximately 7–8 g of a 0.5% solution of the test polymer in water was placed in a 60×15 mm tared glass Petri dish. The dishes were then heated for several hours at 100° C. to dryness in an oven and cooled in a desiccator. The dishes with the dried material were weighed ($m_i$) and allowed to stand at 25° C. for 8 days at ambient humidity in the laboratory. The dishes were then reweighed ($m_f$), and the mass gain was presumed to be due to moisture pick-up, thus measuring the humectancy of the polymer. The percentage of the moisture absorbed (% mass gain) is calculated using the formula:

$$\% \text{ moisture absorbed} = \left(\frac{m_f - m_i}{m_i}\right) \times 100$$

where $m_i$=the initial mass immediately after drying, and $m_f$=the final mass after standing for eight days.

Because the tests are run at different times of the year, the absolute numbers for a particular polymer may exhibit some variability, but the trends and rankings are consistent. Sodium hyaluronate (fermentation grade), an excellent biocompatible humectant, and sodium pyrrolidone carboxylate, a commercial humectant also used in cosmetics, were used as standards for comparison. The chitosonium polymers of this invention (chitosonium pyrrolidone carboxylate, nicotinate, and mixed salt) were superior to other chitosonium polymers tested, and clearly superior to sodium pyrrolidone carboxylate. Thus, one would expect these chitosonium polymers to be excellent humectants and moisturizers in cosmetic, personal care, and biomedical applications. The compositions also display substantivity to keratinous substrates.

TABLE II

MOISTURE ABSORPTION (HUMECTANCY) TESTING
% Moisture absorbed at 25° C.
after 8 days at ambient humidity

| Polymer | Experiment 1 | 2 | 3 | 4 |
|---|---|---|---|---|
| Sodium hyaluronate | 18.0% | 29.1% | 27.5% | 13.0% |
| Chitosonium pyrrolidone carboxylate | 12.6% | 17.8% | — | 9.4% |
| Chitosonium nicotinate | 11.6% | — | — | — |
| Chitosonium nicotinate/PCA | 11.3% | 16.9% | 18.8% | — |
| Chitosonium salicylate | 9.7% | 10.5% | — | — |
| Chitosonium glutamate | 9.6% | — | — | 8.2% |
| Chitosonium malate | 9.5% | — | — | — |
| Sodium pyrrolidone carboxylate | 3.7% | 2.7% | 3.1% | 2.0% |

EXAMPLE 15

PREPARATION OF CHITOSONIUM NICOTINATE

NOTE: Nicotinic acid and 3-Pyridinecarboxylic acid (CAS registry number 59-67-6) are chemical names for niacin, also called vitamin $B_3$.

A 250 ml, three-necked round bottomed flask was fitted with a stirring addle and motor, a Friedrich condenser, an addition funnel, and a thermometer. The flask was charged with 5.00 g of commercial chitosan (ground to pass a 0.5 mm screen, same material described in Example 17) and 50 ml of acetone. While stirring the slurry, it was heated to 50° C. Then a solution of 3.82 g of nicotinic acid (Aldrich Chemical Company) in 35 ml of distilled water and 50 ml of acetone was added to the chitosan slurry. This nicotinic acid, water, and acetone mixture needs to be heated to affect dissolution. The slurry was then heated at reflux for 45 minutes.

After cooling to room temperature, the polymer was collected by vacuum filtration and washed in a Waring blender twice with 300 ml of acetone, and dried in vacuo to give 7.55 g of a granular tan solid. The DS of nicotinate, as measured by mass gain of the product (corrected for volatiles), was found to be 0.79; the Brookfield viscosity of the polymer (1% aqueous solution at 25° C. and 30 rpm) was found to be 879 cP. The polymer was readily soluble in water to give a clear, colorless solution essentially free of insoluble matter. Heating the mixture to 60° C. accelerates the dissolution process.

EXAMPLE 16

PREPARATION OF THE MIXED SALT OF NICOTINIC AND PYRROLIDONE CARBOXYLIC ACIDS WITH CHITOSAN

A 500 ml, three-necked round bottomed flask was fitted with a stirring paddle and motor, a Friedrich condenser, and an addition funnel. The flask was charged with 9.70 g (contained) of chitosan (ground to pass a 0.5 mm screen) and 100 ml of acetone. The chitosan used was obtained from a commercial source with a degree of deacetylation of about 80% and a 1% Brookfield viscosity (as measured in 1% aqueous acetic acid solution at 20° C. and 30 rpm) of about 5000 cP. The chitosan slurry was stirred and heated to reflux. In a beaker, 2.30 g of 2-pyrrolidone-5-carboxylic acid, 6.80 g of nicotinic acid (both from Aldrich Chemical Company), 100 ml of acetone, and 70 ml of water were mixed together and heated until all of the solid had dissolved. The hot solution was added to the refluxing chitosan slurry, and the mixture was allowed to reflux for 1 hour.

After refluxing for 1 hour, the hot slurry was vacuum-filtered, and the solid polymer was washed in a Waring blender twice, with 300 ml of acetone. The tan solid was dried overnight in vacuo to afford 16.01 g of product. The DS of nicotinate was determined spectrophotometrically ($\lambda$max.=266 mm, $\epsilon$=3000 $M^{-1}cm^{-1}$), and the DS of pyrrolidone The polymer was completely soluble in water to give a clear, slightly amber solution essentially free of insoluble matter, and the Brookfield viscosity of the polymer (1% aqueous solution at 25° C. and 30 rpm) was found to be 802 cP.

EXAMPLE 17

PREPARATION OF GLYCIDYLTRIMETHYLAMMONIUM CHLORIDE/ETHYLENE OXIDE MODIFIED CHITOSAN USING THE ACID DECRYSTALLIZATION PROCEDURE

A 500 ml resin kettle was fitted with a stirring paddle and motor, a dry ice/acetone condenser connected to a mineral oil bubbler, a pressure-equalizing addition funnel, a subsurface nitrogen sparge tube, and a rubber serum cap. The kettle was charged with 10.00 g (contained) of chitosan (ground to pass a 0.5 mm screen) and 100 ml of isopropyl alcohol. The chitosan used was obtained from a commercial source with a degree of deacetylation of about 80% and a 1% Brookfield viscosity (in 1% aqueous acetic solution at 20° C. and 30 rpm) of about 2000 cP. While stirring the slurry, the mixture was deoxygenated by using a subsurface nitrogen purge, throughout the course of the reaction.

After stirring the slurry and purging for 15 minutes, a solution of 8.00 g of 2-pyrrolidone-5carboxylic acid (Aldrich Chemical Company) in 32.00 of distilled water was added dropwise over a few minutes, followed by a solution of 42 ml of isopropyl alcohol and 36 ml of distilled water. The chitosan particles became swollen, and the slurry viscosity increased. After 1 hour of stirring (under nitrogen), 7.50 g of 50% aqueous sodium hydroxide were added to the slurry via syringe. The slurry was stirred for 45 minutes (under nitrogen).

A solution of 12.1 g of freshly distilled ethylene oxide in 10.00 g of isopropyl alcohol was added to the slurry, followed by 12.0 g of 72% aqueous glycidyltrimethylammonium chloride. Heat was applied, and the mixture was allowed to reflux for 10 hours under nitrogen. The slurry was then cooled to room temperature, and a solution of 4.20 g of 2-pyrrolidone-5-carboxylic acid in 10.00 g of water was added to neutralize the causticized slurry. The polymer was collected by vacuum filtration, washed in a Waring blender (twice with 500 ml of 4:1 (by volume) isopropyl alcohol/water, and once with 500 ml pure isopropyl alcohol), and dried in vacuo at 50° C. to afford 21.67 g of polymer as a granular beige solid. The polymer was readily soluble in water to give a solution free of particulates and insolubles, and no polymer precipitation was observed in alkaline (pH=12) or acidic (pH =1) solution. The Brookfield viscosity of the polymer (1% aqueous solution at 20° C. and 30 rpm) was found to be 106 cP.

To demonstrate the efficacy of the method of this invention in producing uniform, completely soluble covalent chitosan derivatives, the above procedure was repeated exactly, except that the initial charge of 8.00 g of 2-pyrrolidone-5-carboxylic acid was omitted, and the 50% aqueous sodium hydroxide charge was reduced from 7.50 g to 2.54 g. The resulting polymer was only partly soluble in water, with a high degree of insoluble matter present.

EXAMPLE 18

USE OF AQUEOUS CHITOSONIUM POLYMERS IN TWO COMPONENT SPRAYABLE WOUND DRESSINGS

A solution of chitosonium pyrrolidone carboxylate was prepared by dissolving 2.0 g of chitosan (low molecular weight, 1% solution viscosity in 1% aqueous acetic acid of less than 100 cP at 30 rpm) and 1.2 g of 2-pyrrolidone-5-carboxylic acid in 98 g of sterile water. Alternately, 3.2 g of solid chitosonium pyrrolidone carboxylate; prepared by spray drying, freeze drying, the method of this invention, or other appropriate method, can be dissolved directly in 98 g of sterile water. The polymer solution is then charged to a plastic pump spray bottle (A). A second solution of sodium alginate (Sigma Chemical Company) was prepared by dissolving 0.33 g of sodium alginate in 99 g of sterile water, and this solution was charged to a second plastic pump spray bottle (B).

Clean glass plates heated to 37° C. were used as the substrate to model a typical dermal surface. While warmed at 37° C., solution A was sprayed on and allowed to dry for a few minutes, then solution B was sprayed on and also allowed to dry for a few minutes. A control experiment was conducted in which only solution A was sprayed on the substrate, and solution B was omitted. The plates were then immersed in distilled water at 25° C. and allowed to stand for 30 minutes, to simulate the effect of body fluid on the dressing.

The plate coated only with solution A (control) exhibited complete dissolution of the film from the surface of the plate, demonstrating loss of the film dressing in water. However, the plate coated with both solutions A and B gave a polyelectrolyte composite film which retained adhesion to the surface of the plate even when totally immersed in water. This behavior of adhesion in water is highly desirable in a wound dressing. The compatibility of chitosonium polymers with tissue is well documented. Although this example uses chitosonium pyrrolidone carboxylate, other chitosonium salts such as itaconate, ascorbate, nicotinate, lactate, acetate, glutamate, and aspartate would be equally suitable. Other suitable anionic polymers such as sodium hyaluronate, chondroitin sulfate, keratan sulfate, carrageenan, heparin, and carboxymethylcellulose can be used instead of sodium alginate.

EXAMPLE 19

PREPARATION AND OXIDATIVE CROSS-LINKING OF CHITOSONIUM ASCORBATE

A 250 ml, three-necked round bottomed flask was fitted with a stirring paddle and motor, and two rubber serum caps. The flask was charged with 6.0 g of commercial chitosan (ground to pass a 0.5 mm screen, same material described in Example 17) and 60 ml of isopropyl alcohol, and the flask was fitted with a subsurface nitrogen feed (syringe needle) and a mineral oil bubbler as an outlet. Because of the oxidative sensitivity of the product, the reaction and the work-up were conducted under nitrogen, and all dissolved oxygen was removed from all solutions and diluents by purging with nitrogen for 30 minutes or longer.

While stirring the slurry under nitrogen for 1 hour, a solution of 6.62 g of L-ascorbic acid (Aldrich Chemical Company) in 25 ml of distilled water was prepared. This solution was then added to the chitosan slurry by syringe, and after 30 minutes, a solution of 26 ml of isopropyl alcohol and 11 ml of distilled water was added.

After stirring two additional hours, the flask was transferred to a GLOVE-BAG ® ($I^2R$), and the polymer was recovered by vacuum-filtration under nitrogen. The polymer was washed under nitrogen once with a solution of 160 ml of isopropyl alcohol and 40 ml of water, and once with 200 ml of isopropyl alcohol. The light tan solid was briefly dried under nitrogen, and a 2% solution of the polymer in deoxygenated water was prepared. Films were cast on tin plates at ambient temperature using this solution: some films were allowed to dry in air, while others were dried under nitrogen. The films dried under nitrogen remained colorless and were readily soluble in water, while the films dried in air exhibited a yellowish tint and were insoluble in water, even on prolonged heating in water. Although the mechanism of insolubilization is not well understood, it is presumed to be oxidative because of the importance of oxygen being present during film insolubilization. Such a room temperature, air curing polymer system would have utility in personal care and biomedical applications such as wound dressings, skin care, pharmaceutical delivery systems, slow-release for fragrance, cosmetic, or medicament delivery, among others.

EXAMPLE 20

SALT TOLERANCE OF CHITOSONIUM PYRROLIDONE CARBOXYLATE

The salt tolerance of chitosonium pyrrolidone carboxylate and chitosonium glutamate was tested in aqueous sodium chloride solution. 40 g of a 1.25% aqueous solution of the polymer were diluted with 10 g of 4.25% aqueous sodium chloride to give a final solution composition of 1% aqueous polymer in 0.85% saline solution (0.85% NaCl is biological saline concentration). Upon standing for a few days, the chitosonium pyrrolidone carboxylate/saline solution was still clear, viscous, and homogeneous, while the chitosonium glutamate/saline solution was quite hazy, with much white precipitate. This experiment clearly demonstrates the instability of chitosonium glutamate in solutions of biological saline and, in contrast, the salt tolerance of chitosonium pyrrolidone carboxylate solutions. The stability of chitosonium pyrrolidone carboxylate in saline solution is an important property for various applications including cosmetic formulations, other personal care applications and biomedical uses.

What is claimed is:

1. A heterogeneous method for preparing chitin or chitosan derivative from highly crystalline, partially deacetylated chitin or chitosan which comprises the steps of:
   (a) forming a mixture of a pulverulent, partially deacetylated chitin or chitosan and
      (1) a diluent medium in which the chitin or chitosan is swellable but essentially insoluble; the medium comprised of:
         (i) an inert, water soluble polar organic diluent in which the chitin or chitosan is insoluble and the chitin or chitosan derivative is insoluble;
         (ii) at least one organic acid which is at least partially soluble in water, is sufficiently acidic to form the ammonium salt of the chitin or chitosan and yet not sufficiently acidic to cause hydrolysis of the chitin or chitosan or the chitin or chitosan derivative, and which is present in an amount sufficient to protonate the reactive sites of the decacetylated chitin or chitosan;
      (2) water in an amount in excess of the amount of organic acid and up to about 65 weight percent of the medium;
   (b) agitating the mixture at a temperature and for a period of time to effect at least partial decrystallization; and
   (c) recovering the chitin or chitosan derivative from the mixture.
2. The method of claim 1 wherein the chitin or chitosan is chitosan.
3. The method of claim 1 wherein the chitin or chitosan is in powdered or flake form.
4. The method of claim 1 wherein the chitin or chitosan has been deacetylated to about 60 to about 90 percent and has a molecular weight of from about 10,000 to about 5 million.
5. The method of claim 1 wherein the diluent is an alcohol.
6. The method of claim 5 wherein the diluent is methanol, ethanol, n-propanol, isopropanol, t-butanol or mixtures thereof.
7. The method of claim 1 wherein the acid is represented by the formula:

$$R\text{-}(COOH)_n$$

wherein n has a value of 1 or 2 and R represents a mono- or divalent organic radical composed of carbon, hydrogen and up to one or more oxygen, nitrogen and sulfur atoms.
8. The method of claim 7 wherein the acid is formic, acetic, N-acetylglycine, acetylsalicylic, furamic, glycolic, iminodiacetic, itaconic, DL-lactic, maleic, DL-malic, nicotinic, 2-pyrrolidone-5-carboxylic, salicylic, succinamic, succinic acid, ascorbic, aspartic, glutamic, glutaric, malonic, pyruvic, sulfonyldiacetic, thiodiacetic or thioglycolic acid or mixtures thereof.
9. The method of claim 8 wherein the acid is acetic, 2-pyrrolidone-5-carboxylic, succinic, aspartic, glutamic, nicotinic or itaconic acid or mixtures thereof.
10. The method of claim 1 wherein said chitosan derivative is recovered from said mixture by dewatering with a water-soluble, organic diluent and dried.
11. The method of claim 1 wherein after swelling and decrystallization a base is added to said mixture to neutralize the acid and form causticized, amorphous chitin or chitosan.
12. The causticized chitin or chitosan produced by the process of claim 11.
13. The method of claim 11 wherein the causticized chitosan is further reacted with at least one electrophile to provide covalently-modified chitosan derivatives.
14. The method of claim 13 wherein the electrophile is ethylene oxide, propylene oxide, ethyl chloride, methyl chloride, chloroacetic acid or its salt, a glycidyl trialkyl ammonium salt, 3-chloro-2-hydroxy propyl trialkylammonium salt, N-dodecyl-N,N-dimethylammonium 3-chloro-2-hydroxypropane or mixtures thereof.
15. The method of claim 13, wherein the causticized chitosan is further reacted with at least two electrophiles.
16. A chitin or chitosan derivative produced by the process of claim 1.
17. A film comprising suitable film additives and the chitin or chitosan derivative of claim 16.
18. A personal care formulation comprising suitable carrier and an effective amount of the chitin or chitosan derivative of claim 16.
19. A sunscreen formulation comprising sunscreen agent and an effective amount of the chitin or chitosan derivative of claim 16.
20. The film of claim 17 in the form of a membrane useful in fluid separation.
21. Chitosonium salt of an acid selected from the group consisting of:
    2-pyrrolidone-5-carboxylic, itaconic and nicotinic acids.
22. A personal care composition containing an effective amount of a chitosonium salt of claim 21.

* * * * *

UNITED STATES PATENT AND TRADEMARK OFFICE
CERTIFICATE OF CORRECTION

PATENT NO. : 4,929,722

DATED : May 29, 1990

INVENTOR(S) : Partain et al.

It is certified that error appears in the above-identified patent and that said Letters Patent is hereby corrected as shown below:

ON TITLE PAGE:

Abstract, line 2, change "chitosen" to -- chitosan --.
Column 14, line 17, change "Salicyclic" to -- Salicylic --.
Column 18, line 50 after "$cm^{-1}$)", add -- to be 0.57 --.
Column 18, line 51 after "pyrrolidone", add -- carboxylate was determined by mass balance to be 0.26 --.
Column 19, line 10, change "2-pyrrolidone-5carboxylic" to -- 2-pyrrolidone-5-carboxylic --.
Column 21, line 52 (line 20 of Claim 1), change "decacetylated" to -- deacetylated --.

Signed and Sealed this

Third Day of December, 1991

Attest:

HARRY F. MANBECK, JR.

*Attesting Officer*  *Commissioner of Patents and Trademarks*